US012678119B2

(12) United States Patent
Matsumoto et al.

(10) Patent No.: US 12,678,119 B2
(45) Date of Patent: Jul. 14, 2026

(54) X-RAY DIAGNOSTIC APPARATUS, X-RAY CONDITION DETERMINATION METHOD, AND NON-TRANSITORY COMPUTER-READABLE MEDIUM

(71) Applicant: Canon Kabushiki Kaisha, Tokyo (JP)

(72) Inventors: Masanori Matsumoto, Nasushiobara (JP); Saki Hashimoto, Nasushiobara (JP); Keisuke Sugawara, Otawara (JP); Shingo Abe, Nasushiobara (JP); Akio Tetsuka, Shioya (JP); Yusuke Kanno, Sendai (JP); Yoshiyuki Sato, Nasushiobara (JP); Hisayuki Uehara, Otawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 348 days.

(21) Appl. No.: 18/357,424

(22) Filed: Jul. 24, 2023

(65) Prior Publication Data
US 2024/0032882 A1     Feb. 1, 2024

(30) Foreign Application Priority Data
Jul. 28, 2022     (JP) ................................ 2022-120716

(51) Int. Cl.
*A61B 6/00*          (2024.01)
*A61B 6/46*          (2024.01)
*G06T 7/00*          (2017.01)
(52) U.S. Cl.
CPC .............. *A61B 6/545* (2013.01); *A61B 6/469* (2013.01); *G06T 7/0012* (2013.01); *G06T 2207/10116* (2013.01)

(58) Field of Classification Search
None
See application file for complete search history.

(56) References Cited

U.S. PATENT DOCUMENTS 12,274,571 B2 *   4/2025   Hayashida ............. A61B 6/542
2002/0085672 A1    7/2002   Ganin et al.
(Continued)

FOREIGN PATENT DOCUMENTS

DE          101 64 170 A1      8/2002
JP          2015228994      * 12/2015
(Continued)

OTHER PUBLICATIONS

Extended European Search Report Issued Dec. 22, 2023 in European Application 23188214.3, 7 pages.

*Primary Examiner* — Nancy Bitar
(74) *Attorney, Agent, or Firm* — Oblon, McClelland, Maier & Neustadt, L.L.P.

(57)          ABSTRACT

According to one embodiment, an X-ray diagnostic apparatus includes processing circuitry. The processing circuitry sets a plurality of ROIs in a first X-ray image. The processing circuitry calculates a statistical value for each ROI based on a plurality of values of pixels included in each ROI, thereby obtaining a plurality of statistical values. The processing circuitry acquires a threshold value for each statistical value. The processing circuitry determines a set of X-ray conditions relating to capturing of a second X-ray image subsequent to the first X-ray image based on the statistical value and the threshold value relating to each ROI.

18 Claims, 9 Drawing Sheets

(56) References Cited

U.S. PATENT DOCUMENTS

2015/0359498  A1 *  12/2015  Zou ........................ A61B 6/469
                                                        378/62
2020/0323505  A1 *  10/2020  Tanaka ................. A61B 6/4441
2023/0148985  A1      5/2023  Kanno et al.

FOREIGN PATENT DOCUMENTS

JP          2023-73628  A     5/2023
WO          2015/195515  A2   12/2015

* cited by examiner

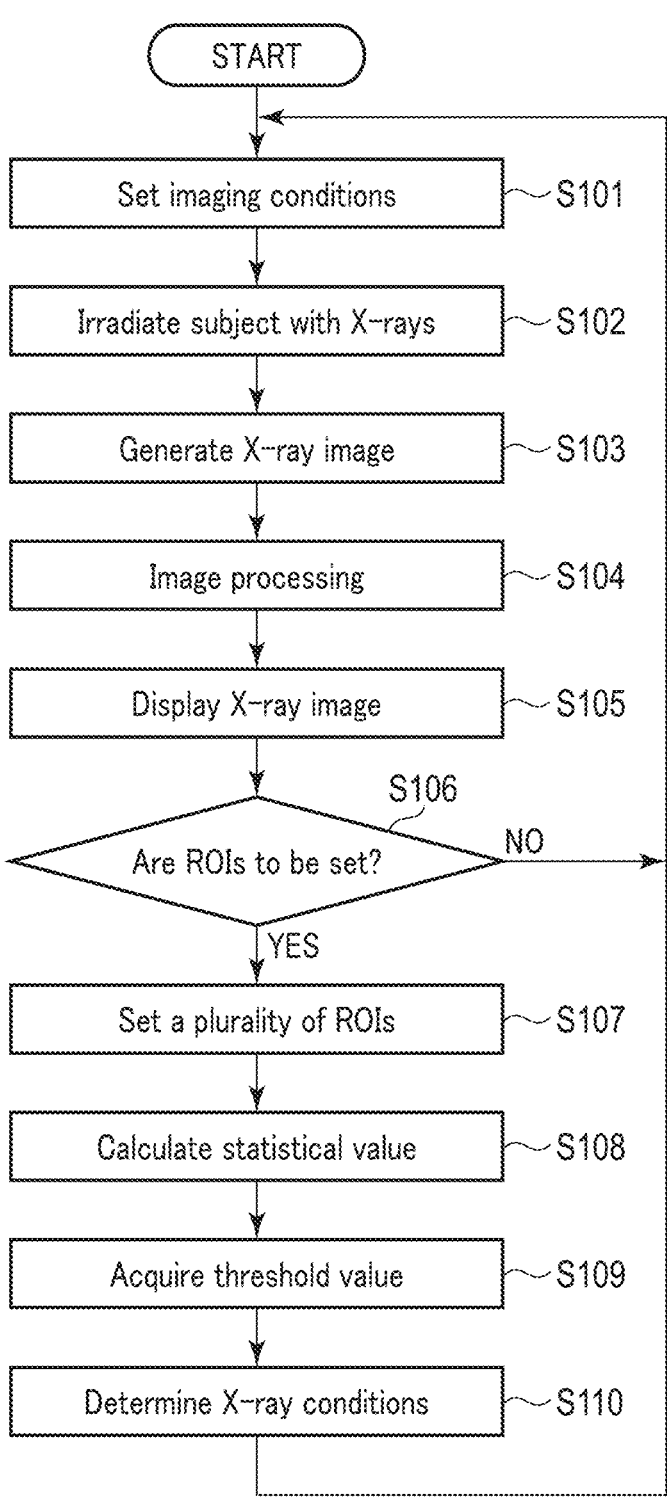
F I G. 2

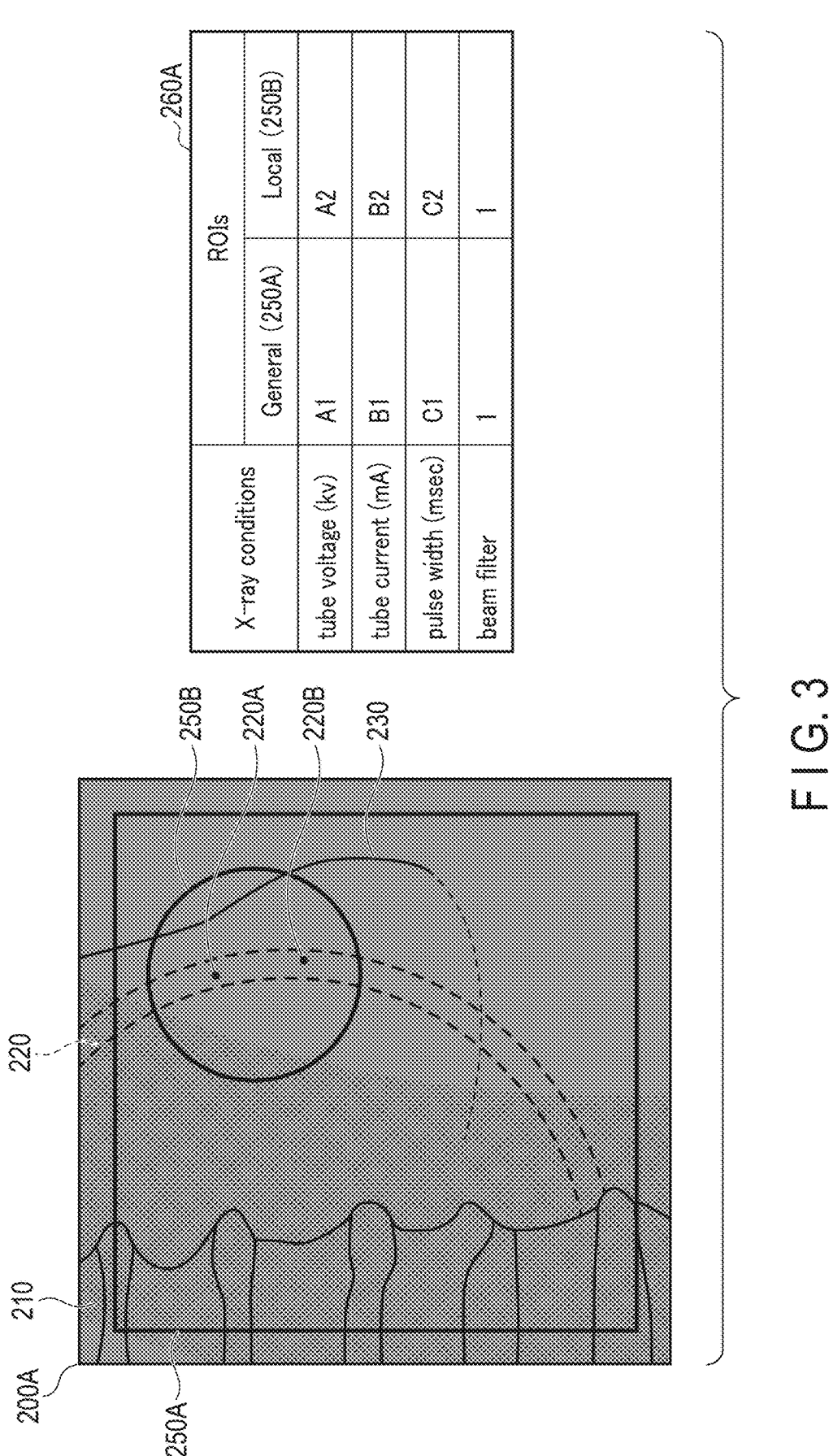
| X-ray conditions | ROIs | |
|---|---|---|
| | General (250A) | Local (250B) |
| tube voltage (kv) | A1 | A2 |
| tube current (mA) | B1 | B2 |
| pulse width (msec) | C1 | C2 |
| beam filter | 1 | 1 |
F I G. 3

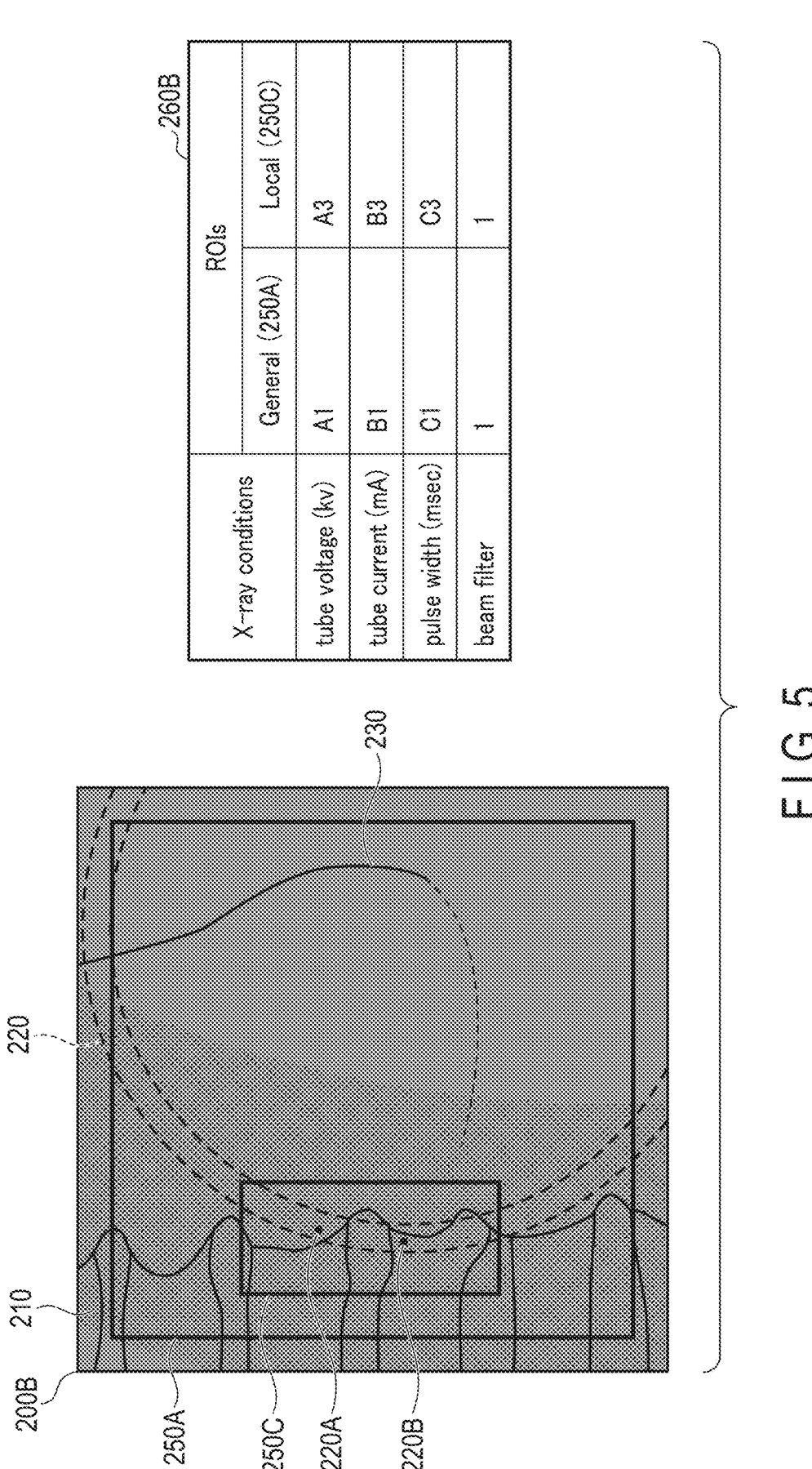
F I G. 5

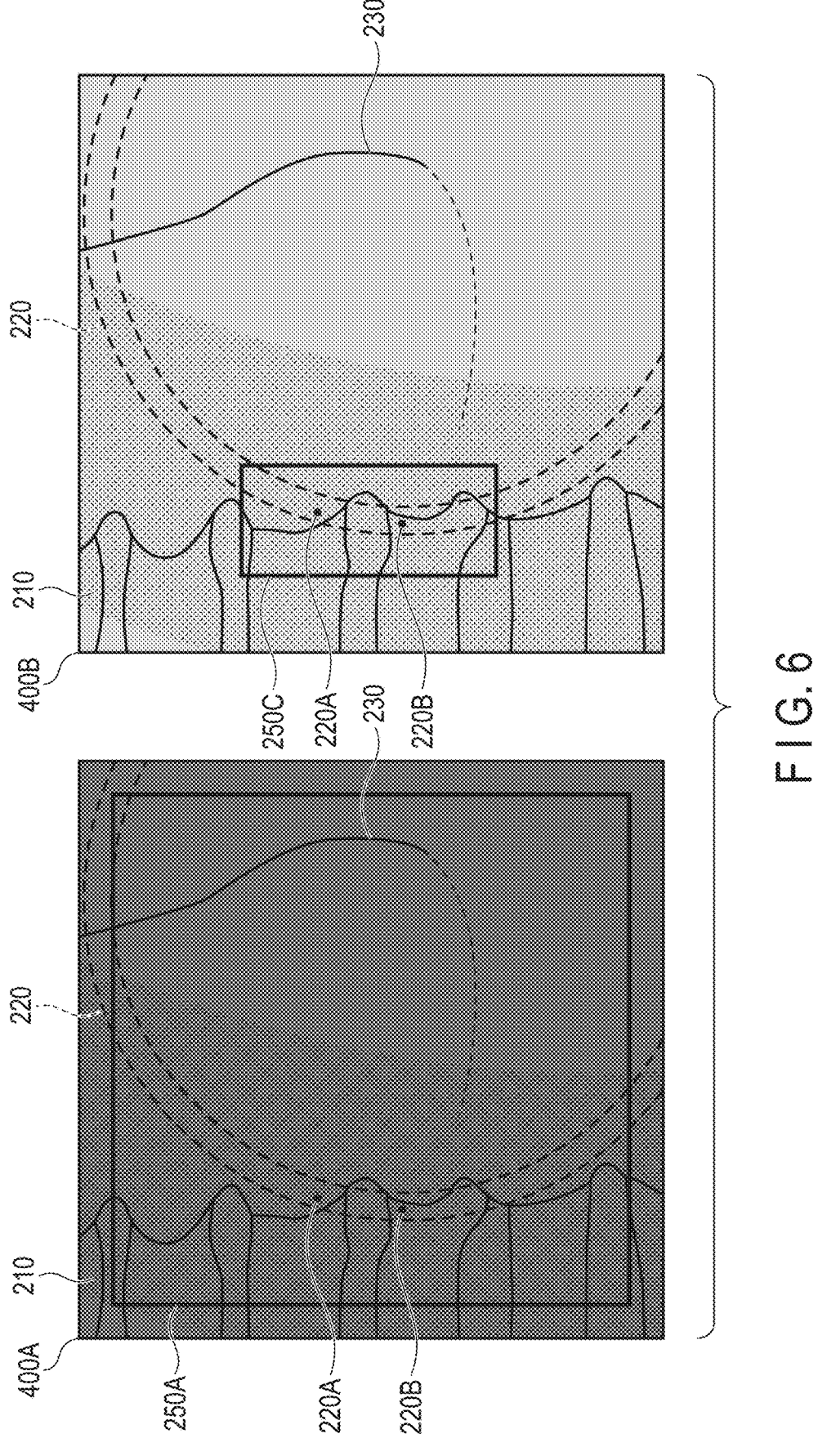
F I G . 6

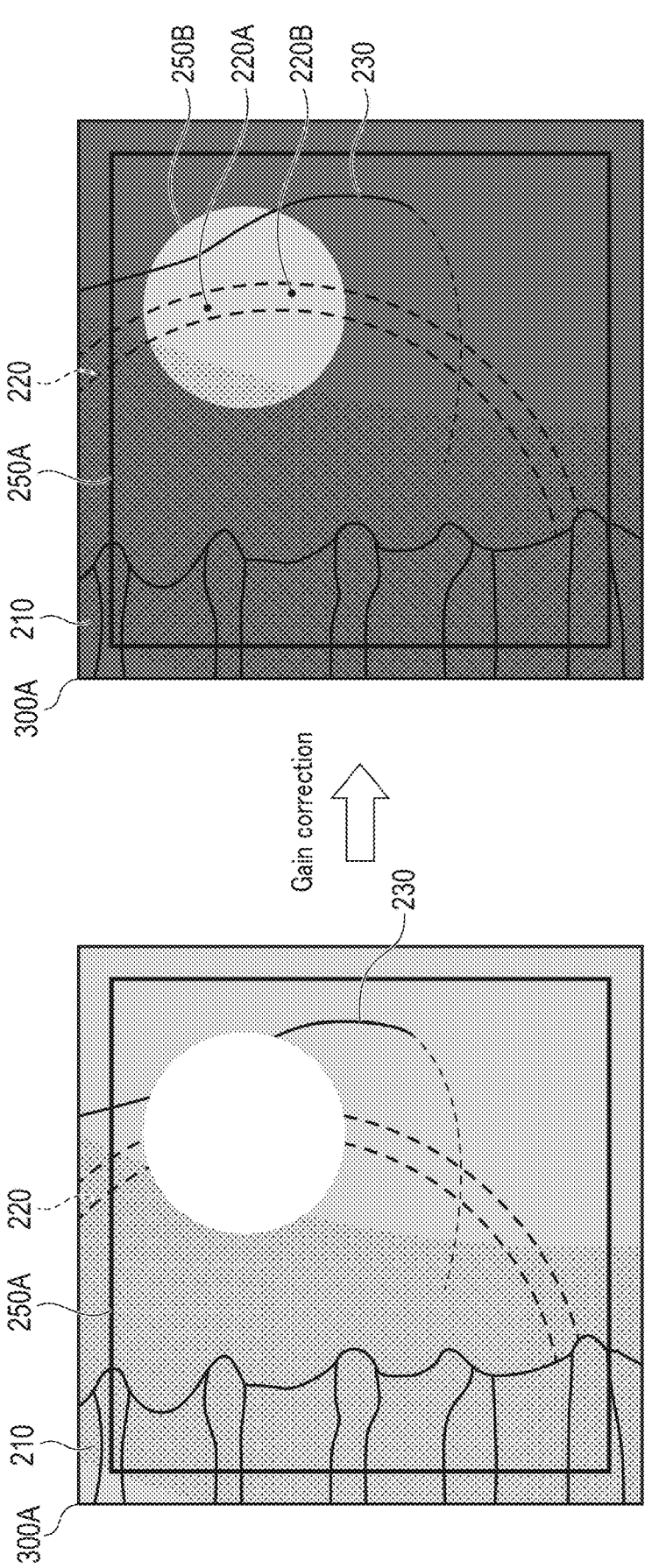
F I G. 7

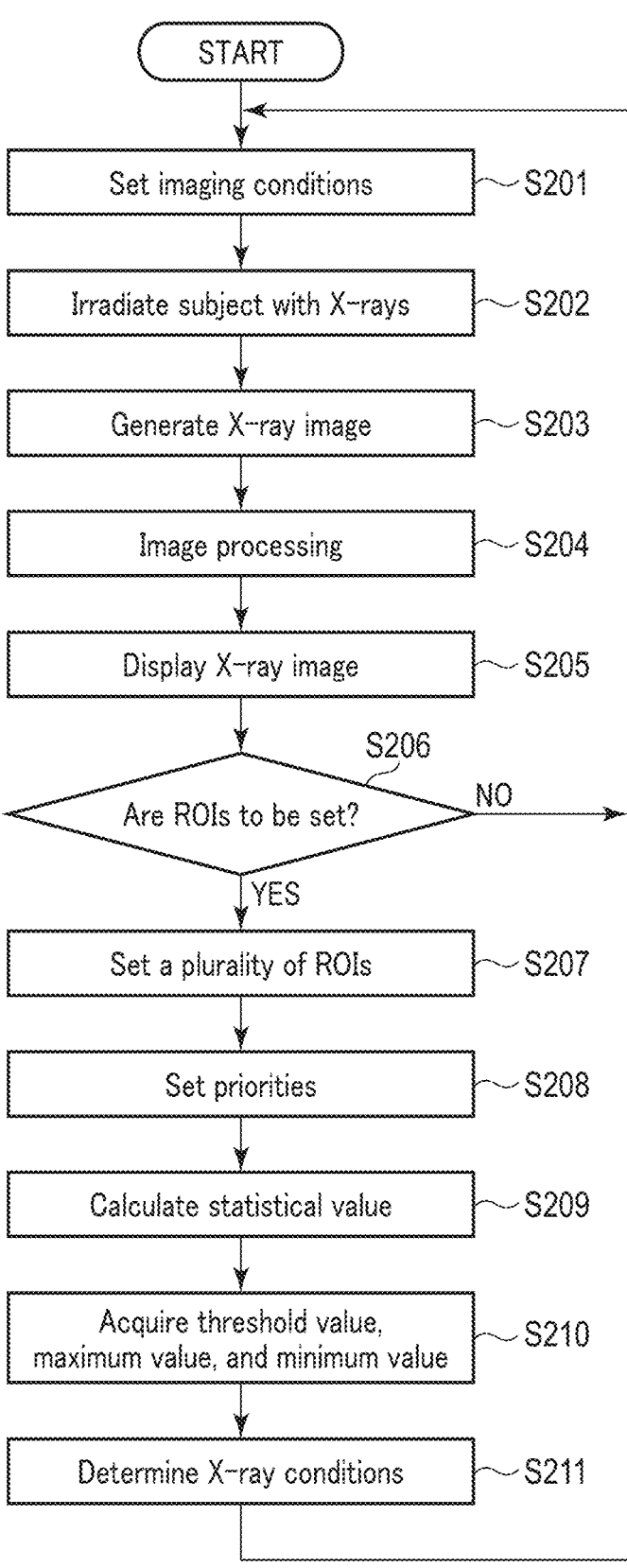
F I G. 8

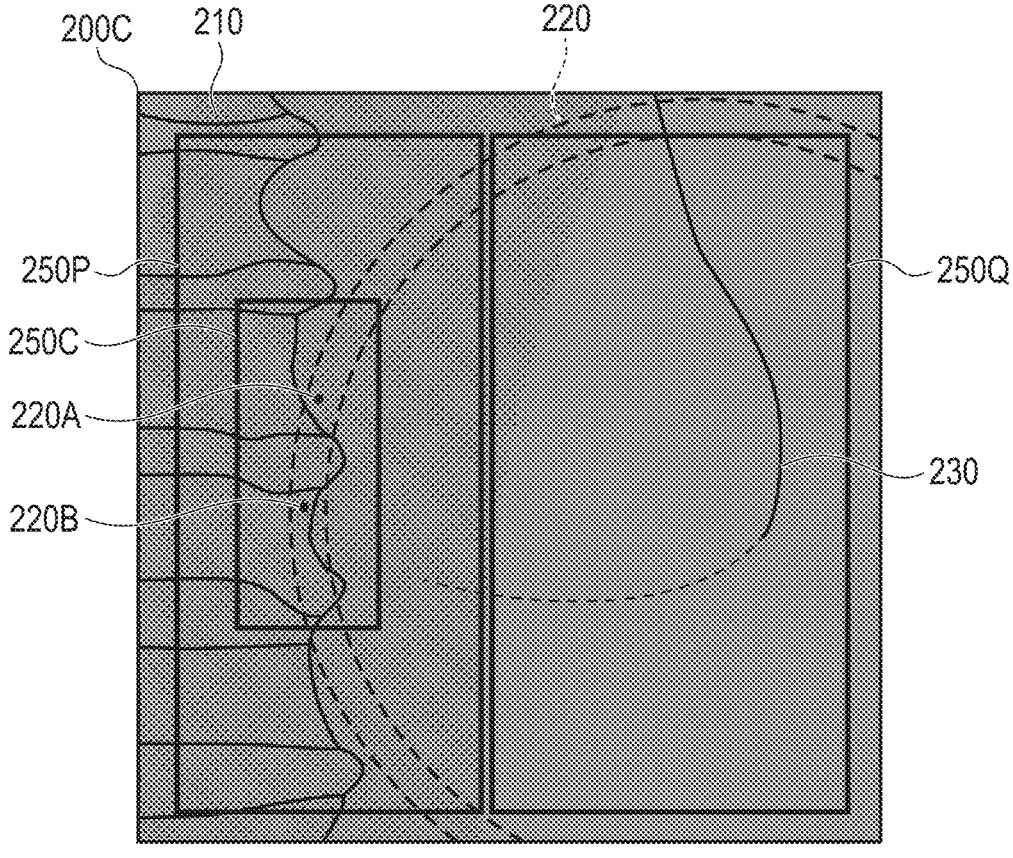
F I G. 9

X-RAY DIAGNOSTIC APPARATUS, X-RAY CONDITION DETERMINATION METHOD, AND NON-TRANSITORY COMPUTER-READABLE MEDIUM

CROSS-REFERENCE TO RELATED APPLICATION

This application is based upon and claims the benefit of priority from Japanese Patent Application No. 2022-120716, filed Jul. 28, 2022, the entire contents of which are incorporated herein by reference.

FIELD

Embodiments described herein relate generally to an X-ray diagnostic apparatus, an X-ray condition determination method, and a non-transitory computer-readable medium.

BACKGROUND

Recently adopted techniques for controlling X-ray conditions using X-ray diagnostic apparatuses include automatic brightness control (ABC), which maintains the brightness in a region of interest (ROI) set on an X-ray image to be constant, and contrast-to-noise ratio (CNR) control, which maintains the noise level in an ROI to be constant. Such an ROI may be set either over an entire region of the X-ray image, or may be locally set at a limited position of a target photographed in the X-ray image. An X-ray diagnostic apparatus performs ABC or CNR control based on the set ROI, thereby determining an optimum set of X-ray conditions relating to capturing of the next X-ray image, and capturing the X-ray image.

If, for example, a local ROI is set at the position of a target in a relatively dark region (e.g., a portion with a large subject thickness) on an X-ray image, the X-ray diagnostic apparatus performs ABC or CNR control to secure an appropriate dose for the ROI and to secure a sufficient dose for the entire X-ray image. On the other hand, if a local ROI is set at the position of a target in a relatively bright region (e.g., a portion with a small subject thickness) on an X-ray image, the X-ray diagnostic apparatus can secure an appropriate dose for the ROI, but may not be able to secure a sufficient dose for the entire X-ray image. This results in an insufficient dose for the entire X-ray image, causing a decrease in visibility of an object in the relatively dark region on the X-ray image.

BRIEF DESCRIPTION OF THE DRAWINGS

FIG. 2 shows an operation example of the X-ray diagnostic apparatus according to the first embodiment.

FIG. 3 shows a first example relating to setting of a plurality of ROIs and calculation of a plurality of sets of X-ray conditions by the X-ray diagnostic apparatus according to the first embodiment.

FIG. 5 shows a second example relating to setting of a plurality of ROIs and calculation of a plurality of sets of X-ray conditions by the X-ray diagnostic apparatus according to the first embodiment.

FIG. 6 shows a display example of an X-ray image based on the second example of FIG. 5.

FIG. 7 shows an example of gain correction of an X-ray image upon occurrence of a halation.

FIG. 8 shows an operation example of an X-ray diagnostic apparatus according to a second embodiment.

FIG. 9 shows an example of a method of setting a plurality of ROIs according to another embodiment.

DETAILED DESCRIPTION

In general, according to one embodiment, an X-ray diagnostic apparatus includes processing circuitry. The processing circuitry sets a plurality of ROIs in a first X-ray image. The processing circuitry calculates a statistical value relating to each of the ROIs based on a plurality of values of pixels included in each of the ROIs, thereby obtaining a plurality of statistical values. The processing circuitry acquires a threshold value relating to each of the statistical values. The processing circuitry determines a set of X-ray conditions relating to capturing of a second X-ray image subsequent to the first X-ray image based on the statistical value and the threshold value relating to each of the ROIs.

The X-ray diagnostic apparatus, the X-ray condition determination method, and the non-transitory computer-readable medium according to the embodiments will be described with reference to the accompanying drawings. In the embodiments described below, elements assigned the same reference symbols are assumed to perform the same operations, and redundant descriptions will be suitably omitted.

First Embodiment

Figure 1:
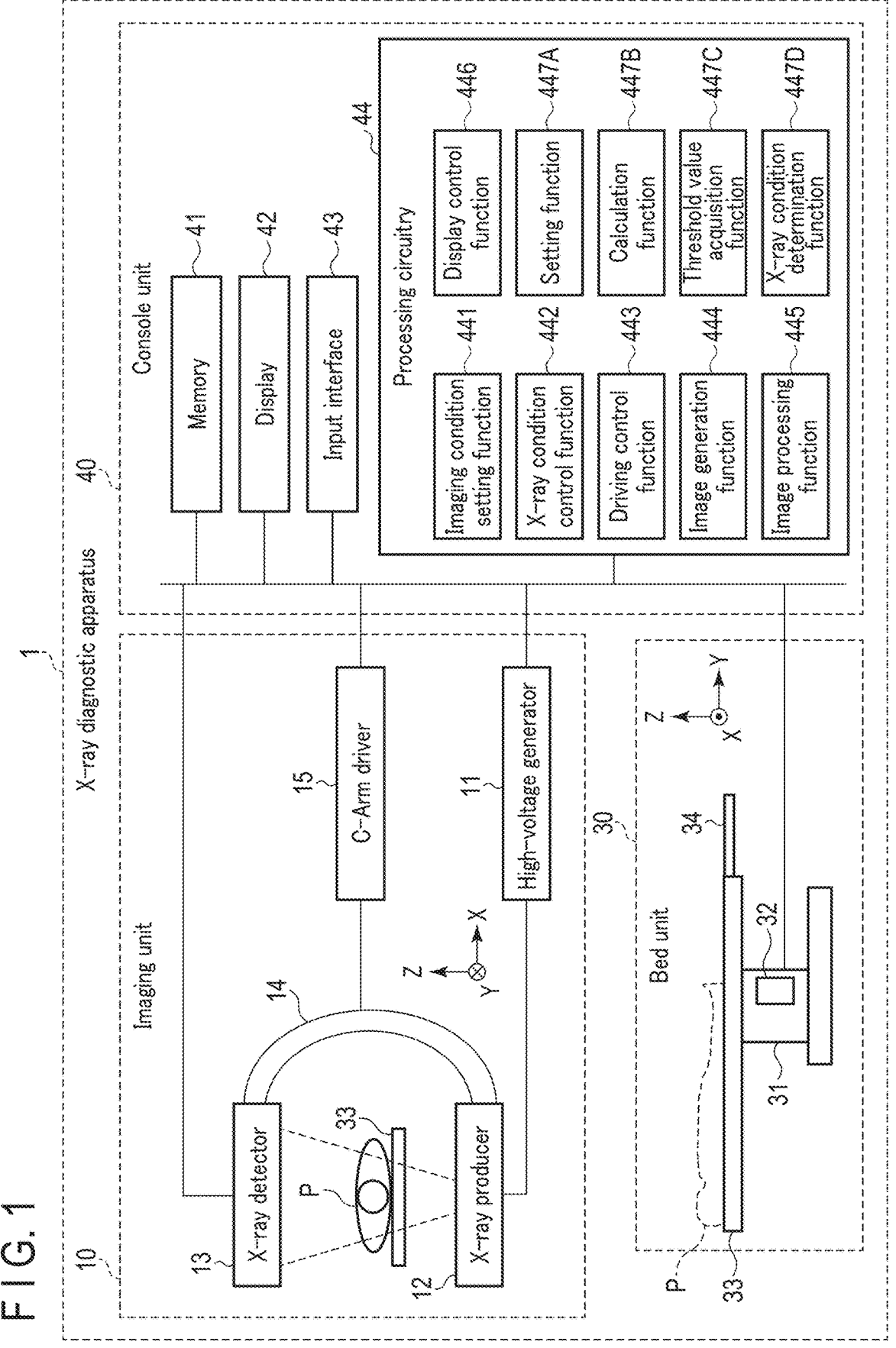
FIG. 1 shows a configuration example of an X-ray diagnostic apparatus according to a first embodiment.

FIG. 1 shows a configuration example of an X-ray diagnostic apparatus 1 according to a first embodiment. For concreteness, it is assumed herein that the X-ray diagnostic apparatus 1 is a C-Arm-type X-ray fluoroscopy diagnostic apparatus. That is, an X-ray image captured by the X-ray diagnostic apparatus 1 refers to an X-ray fluoroscopic image. The X-ray diagnostic apparatus 1 includes, as modules, an imaging unit 10, a bed unit 30, and a console unit 40.

The imaging unit 10 is a module that performs X-ray photofluorography in which a subject P is continuously or intermittently irradiated with a low dose of X-rays. The imaging unit 10 may perform one-shot photography (X-ray photography) of irradiating a subject P with a high dose of X-rays. The imaging unit 10 includes a high-voltage generator 11, an X-ray producer 12, an X-ray detector 13, a C-Arm 14, and a C-Arm driver 15.

The high-voltage generator 11 is a device that applies a high voltage and supplies a filament current to an X-ray tube included in the X-ray producer 12. Specifically, the high-voltage generator 11 generates a high voltage to be applied across a cathode and an anode of the X-ray tube, and supplies the generated high voltage to the X-ray tube. The high-voltage generator 11 may be either a converter type or an inverter type.

The X-ray producer 12 is a mechanism of producing X-rays, and adjusts a radiation quality, a dose, and an irradiation field size of the X-rays. The X-ray producer 12 includes an X-ray tube, and a filter and an X-ray diaphragm for adjusting the X-rays.

The X-ray tube included in the X-ray producer 12 is a vacuum tube that produces X-rays. The X-ray tube is, for example, a rotating-anode-type X-ray tube that produces X-rays by irradiating thermions onto a rotating anode. The X-ray tube includes a bulb, and a filament (cathode) and a metal target (anode) provided in the bulb. The X-ray tube accelerates thermions discharged from the filament (e.g., tungsten) with a high voltage, and lets the accelerated thermions collide with the metal target (e.g., tungsten, molybdenum, or copper), thereby producing X-rays. In this manner, the X-ray tube irradiates the subject P with the X-rays.

The filter included in the X-ray producer 12 regulates the dose, radiation quality, etc. of X-rays to be transmitted therethrough for the purpose of reducing the dose of exposure to the subject P and improving the image quality of X-ray image data. Examples of the filter include X-ray filters of various types, such as a beam filter, a dose-reducing filter, and a compensating filter. The various types of X-ray filters are provided between the X-ray tube and the subject P.

The beam filter is a plate of a metal such as copper, aluminum, etc. Being inserted between the X-ray tube and X-ray diaphragm, the beam filter removes long-wavelength components (soft X-rays) included in continuous-spectrum X-rays with which irradiation has been performed by the X-ray tube according to a thickness (e.g., 0.1 mm to 5 mm) of the beam filter. In other words, the beam filter lets short-wavelength components (hard X-rays) included in the continuous-spectrum X-rays with which irradiation has been performed by the X-ray tube selectively pass therethrough, and increases the radiation quality of (hardens) the X-rays. That is, the beam filter extracts desired energy components by removing, from the X-rays, energy components not required for X-ray diagnosis. In this manner, the beam filter adjusts the radiation quality and the dose of X-rays irradiated by the X-ray tube. The beam filter may be referred to as an additional filter, an X-ray filter, a filtration plate, or a radiation quality filter.

The beam filter according to the present embodiment is configured of four beam filters (filters 1 to 4). The filters 1 to 4 have different thicknesses. Accordingly, the filters 1 to 4 differ in the soft X-ray removal rate (X-ray reduction rate). A thick beam filter (a beam filter with a large thickness) has a high X-ray reduction rate compared to a thin beam filter (a beam filter with a small thickness). The thickness of the filter 1 is smaller than the thickness of the filter 2, and the thickness of the filter 2 is smaller than the thickness of the filter 3, and the thickness of the filter 3 is smaller than the thickness of the filter 4. Accordingly, the X-ray reduction rate of the filter 1 is smaller than the X-ray reduction rate of the filter 2, the X-ray reduction rate of the filter 2 is smaller than the X-ray reduction rate of the filter 3, and the X-ray reduction rate of the filter 3 is smaller than the X-ray reduction rate of the filter 4. It is to be noted that the four beam filters are not necessarily of an identical material, and may be configured of different materials. The beam filters are selected from among a plurality of beam filters according to an input by an operator via an input interface 43 (to be described below) or setting by processing circuitry 44 (to be described below), and inserted between the X-ray tube and the X-ray diaphragm.

The dose-reducing filter attenuates some of the X-rays with which irradiation has been performed by the X-ray tube to make the dose of X-rays with which an area other than an attention area is to be irradiated become lower than the dose of X-rays with which the attention area is to be irradiated, for the purpose of, for example, reducing the dose of radiation to the subject P. The dose-reducing filter may be a filter (punched filter) with an opening at its center. Specifically, the punched filter is a metal plate with a rectangular opening at its center, including a dose-reducing portion for reducing the X-rays on the periphery of the opening. With such a configuration, the punched filter allows the dose of X-rays passing through the metal plate on the periphery of the opening to be reduced, without reducing the dose of X-rays passing through the opening. The dose-reducing filter is also referred to as an "X-ray attenuation filter". On the other hand, the compensating filter attenuates some of the X-rays with which irradiation has been performed by the X-ray tube for the purpose of, for example, suppressing halation.

The X-ray diaphragm included in the X-ray producer 12 is a plate of a metal such as lead. The X-ray diaphragm is provided on a front surface of an X-ray emission window in the X-ray tube. The X-ray diaphragm is configured of, for example, four blades configured of plates of metal such as lead. Such blades are driven by a driving unit (not illustrated) in accordance with an ROI of a subject P input by an operator via an input interface 43 of the console unit 40. By causing the driving unit to slide the blades, the X-ray diaphragm adjusts the region in which the X rays are shielded to a given size. In this manner, the X-ray diaphragm narrows down the X-ray irradiation field in such a manner that the ROI of the subject P is irradiated with the X-rays. If a punched filter is used, the X-ray diaphragm narrows down the X-ray irradiation field to conform to the opening of the punched filter.

The X-ray detector 13 is a mechanism for detecting X-rays with which irradiation has been performed from the X-ray tube included in the X-ray producer 12 and which has been transmitted through the subject P. The X-ray detector 13 includes a flat-panel detector (FPD; hereinafter referred to as "FPD"), a gate driver, and a projection-data generation circuit.

The FPD included in the X-ray detector 13 converts X-rays that have been transmitted through the subject P into electric charge, and accumulates charge obtained by the conversion. The FPD includes a plurality of fine semiconductor detection elements (pixels) two-dimensionally arranged in a row direction and a column direction. For the semiconductor detection element, whichever of a direct conversion type, which converts X-rays directly into electric charge, and an indirect conversion type, which converts X-rays into light with a fluorescent substance and converts the light obtained by the conversion into electric charge, may be used. In the former case, each direct-conversion-type semiconductor detection element includes a photoelectric film that generates electric charge in accordance with the dose of incident X-rays, a photodiode (PD) that accumulates electric charge generated in the photoelectric film, an amplifier circuit that amplifies the electric charge, and an A/D converter that converts the amplified electric charge into a digital signal. The digital signal is sequentially read by a driving pulse supplied by the gate driver. At this time, the digital signal is read while keeping the electric charge of the pixels corresponding to the digital signal.

The projection-data generation circuit included in the X-ray detector 13 converts a digital signal read in parallel from the FPD in units of rows or columns into a time-sequential serial signal (projection data). The projection-data generation circuit supplies the projection data to the memory 41 of the console unit 40. In this manner, the X-ray detector 13 detects, for each pixel, the X-rays with which irradiation has been performed by the X-ray producer 12, and supplies the generated projection data to the memory 41.

The C-Arm 14 holds the X-ray producer 12 and the X-ray detector 13, with a top 33 of the bed unit 30 interposed therebetween. The C-Arm 14 is rotatable and slidable around each of a plurality of spatial axes. Thereby, the C-Arm 14 images the subject P placed on the top 33 from a given imaging direction.

The C-Arm driver 15 controls motions relating to rotation and sliding of the C-Arm 14. The C-Arm driver 15 includes a plurality of power sources for realizing various motions of the C-Arm 14. In response to a drive signal from the processing circuitry 44 (driving control function 443) of the console unit 40, the C-Arm driver 15 causes the C-Arm 14 to perform various motions.

The bed unit 30 is a module to be moved, with the subject P placed thereon. The bed unit 30 includes a base 31, a bed driving unit 32, a top 33, and a supporting frame 34.

The base 31 is a housing that movably supports the supporting frame 34 in a vertical direction (Z direction). The base 31 is installed on a floor surface, and houses the bed driving unit 32.

The bed driving unit 32 is a motor or an actuator that moves the top 33 on which the subject P is placed. In response to a driving signal from the processing circuitry 44 (driving control function 443) of the console unit 40, the bed driving unit 32 moves the top 33 horizontally (in X and Y directions) or vertically (in a Z direction) with respect to the floor surface. Thereby, the bed driving unit 32 changes the positional relationship between the subject P and the imaging direction. It is to be noted that the bed driving unit 32 may move the supporting frame 34 in a longitudinal direction (Y direction) of the top 33, together with the top 33.

The top 33 is a plate on which the subject P is mounted. The top 33 is provided on an upper surface of the supporting frame 34.

The supporting frame 34 is a frame that movably supports the top 33 in a longitudinal direction (Y direction). The supporting frame 34 is provided on an upper surface of the base 31.

The bed unit 30 may be of a type (single-deck sliding type) in which the top 33 is movable with respect to supporting frame 34, or a type (double-deck sliding type) in which each of the top 33 and the supporting frame 34 are movable with respect to the base 31.

The console unit 40 is a module that controls the entire operation of the X-ray diagnostic apparatus 1. The console unit 40 performs various types of control in response to various input operations from an operator who uses the X-ray diagnostic apparatus 1. The console unit 40 is configured to be separate from the imaging unit 10 and the bed unit 30. The console unit 40 or at least part of the configuration of the console unit 40 may be mounted on the imaging unit 10 or the bed unit 30. The console unit 40, which is in charge of various types of information processing, may also be called a "medical image processing apparatus", or an "information processing apparatus".

The console unit 40 according to the present embodiment performs a plurality of functions on a single console. Alternatively, the console unit 40 may execute a plurality of functions on a plurality of consoles. The console unit 40 includes a memory 41, a display 42, an input interface 43, and processing circuitry 44.

The memory 41 is a storage device that stores various types of information (e.g., X-ray images, programs, data, trained models, statistical values, and threshold values). The memory 41 is, for example, a hard disk drive (HDD), a solid-state drive (SSD), or an integrated circuit (IC). The memory 41 may be a portable storage medium such as a compact disc (CD), a digital versatile disc (DVD), a flash memory, a random access memory (RAM), etc. The memory 41 may be a drive that reads and writes various types of information from and to such a portable storage medium. The storage area of the memory 41 may be either in the X-ray diagnostic apparatus 1, or in an external storage device connected to the X-ray diagnostic apparatus 1 via a network.

The X-ray images stored in the memory 41 are two-dimensional X-ray images or frame images based on two-dimensional projection data obtained by, for example, sequentially storing projection data in units of rows or columns. The programs stored in the memory 41 are, for example, programs executed by the processing circuitry 44. Such programs include a control program and an X-ray condition determination program of the X-ray diagnostic apparatus 1. The data stored in the memory 41 is, for example, projection data output from the X-ray detector 13 of the imaging unit 10, pre-processing data, in-processing data, or post-processing data relating to processing by the processing circuitry 44, or various tables.

The display 42 is a display device that displays various types of information (e.g., X-ray images and a graphical user interface (GUI)). The display 42 is, for example, a cathode-ray tube (CRT) display or a liquid crystal display (LCD). The display 42 may be a desktop-type or a tablet-type display device connected to the console unit 40 to enable communications therebetween.

The input interface 43 receives various input operations from an operator who uses the X-ray diagnostic apparatus 1, converts them into electric signals, and outputs the electric signals obtained by the conversion to the processing circuitry 44. The input interface 43 receives input operations such as subject information, imaging conditions, instructions for moving the C-Arm 14 and the top 33, and setting of the ROI. The input interface 43 is configured of a physical operational component (e.g., a mouse, a keyboard, a trackball, a switch, a foot switch, a button, a joystick, a touchpad, or a touch panel display). The input interface 43 may be a circuit that receives various types of input operations from external input equipment provided separately from the X-ray diagnostic apparatus 1, converts them into electric signals, and outputs the electric signals obtained by the conversion to the processing circuitry 44.

The processing circuitry 44 controls the entire operation of the X-ray diagnostic apparatus 1. The processing circuitry 44 includes at least one processor. The term "processor" used herein means, for example, circuitry such as a central processing unit (CPU), a graphics processing unit (GPU), an application-specific integrated circuit (ASIC), or a programmable logic device (e.g., a simple programmable logic device (SPLD), a complex programmable logic device (CPLD), a field-programmable gate array (FPGA)). If the processor is a CPU, the processor reads and executes programs stored in the memory 41 to realize the functions. If the processor is an ASIC, the functions are directly incorporated into the circuitry of the processor as logic circuitry, instead of the programs being stored in the memory 41. The processor may be configured as a single circuit, or a plurality of independent circuits may be combined and integrated as a single circuit. In the present embodiment, the processing circuitry 44 realizes various functions (e.g., an imaging condition setting function 441, an X-ray condition control function 442, a driving control function 443, an image generation function 444, an image processing function 445, a display control function 446, a setting function 447A, a calculation function 447B, a threshold value acquisition function 447C, and an X-ray condition determination function 447D).

The processing circuitry 44 sets, with the imaging condition setting function 441, conditions (hereinafter referred to as "imaging conditions") relating to capturing of X-ray images of the subject P. A set of imaging conditions includes a set of conditions relating to generation of or irradiation with X-rays (hereinafter referred to as "X-ray conditions"), and a set of conditions relating to an image quality of an X-ray image captured under a predetermined set of X-ray conditions (hereinafter referred to as "image quality conditions").

A set of X-ray conditions includes a tube voltage kV and a tube current mA supplied to the X-ray tube included in the X-ray producer 12, a product (tube current-time product) mAs of a tube current and an irradiation time, a pulse width msec, a pulse rate, a type and a thickness of the beam filter, an X-ray irradiation field size, a focus size, a radiation dose, etc. In other words, a set of X-ray conditions includes various parameters relating to setting of a dose of X-rays with which irradiation is to be performed.

In ABC control, a set of X-ray conditions is changed in such a manner that a mean value (statistical value) of a plurality of values of pixels included in an ROI, for example, becomes identical to or substantially identical to a target value (threshold value) of the ROI. In other words, in ABC control, the X-ray diagnostic apparatus 1 determines a set of X-ray conditions in such a manner that a statistical value of an ROI satisfies a threshold value.

On the other hand, in CNR control, an image quality index (statistical value) estimated based on a plurality of values of pixels included in an ROI, for example, is calculated. Specifically, the X-ray diagnostic apparatus 1 acquires in advance correspondence information in which an imaging geometry of the imaging device (e.g., an X-ray irradiation field size, a Source-to-Image Distance (SID)), a plurality of values of pixels included in an ROI, and a set of X-ray conditions relating to collection of the values of pixels are associated with the estimated image quality index. The X-ray diagnostic apparatus 1 acquires an image quality index by referring to the correspondence information based on an imaging geometry in X-ray irradiation, an SID, and a plurality of values of pixels of an ROI obtained by the X-ray irradiation. The image quality index is, for example, a contrast-to-noise ratio. That is, in CNR control, the X-ray conditions are changed in such a manner that a contrast-to-noise ratio (statistical value) estimated based on a plurality of values of pixels corresponding to an ROI becomes identical to or substantially identical to a target value (threshold value) of the ROI. In other words, in CNR control, the X-ray diagnostic apparatus 1 determines a set of X-ray conditions in such a manner that a statistical value of an ROI satisfies a threshold value.

Alternatively, in CNR control, the statistical value to be calculated may be directly calculated from the X-ray image. For example, in CNR control, a value (contrast value) obtained by subtracting a mean value of a plurality of values of pixels included in an ROI from a mean value of a plurality of values of pixels included in a peripheral region of the ROI is calculated. By dividing the calculated contrast value by a standard deviation of the values of pixels included in the peripheral region, a contrast-to-noise ratio is calculated. That is, in CNR control, the X-ray conditions may be changed in such a manner that a contrast-to-noise ratio (statistical value) relating to an ROI becomes identical to or substantially identical to a target value (threshold value) of the ROI. In other words, in CNR control, the X-ray diagnostic apparatus 1 may determine a set of X-ray conditions in such a manner that a statistical value of an ROI satisfies a threshold value.

A set of image quality conditions includes a spatial resolution of the FPD included in the X-ray detector 13, a binning number, the element size and the number of elements, and the pixel size and the number of pixels (resolution) of the X-ray image. In other words, a set of image quality conditions includes various parameters relating to generation of an X-ray image.

The processing circuitry 44 controls, with the X-ray condition control function 442, a set of X-ray conditions relating to capturing of an X-ray image. Specifically, the processing circuitry 44 controls, based on a set of X-ray conditions set by the imaging condition setting function 441, a tube voltage kV, a tube current-time product mAs, a pulse width msec, a pulse rate, a type and a thickness of the beam filter, etc. in the imaging unit 10 in real time. Thereby, X-rays are generated in accordance with a desired set of X-ray conditions, and used for irradiation. Also, projection data relating to a subject P is obtained.

The processing circuitry 44 performs, with the driving control function 443, control to drive the C-Arm driver 15 of the imaging unit 10 and to drive the bed driving unit 32 of the bed unit 30. Specifically, the processing circuitry 44 generates a drive signal based on information relating to driving of the C-Arm driver 15 and the bed driving unit 32 input from the input interface 43, and generates a drive signal. The processing circuitry 44 outputs the generated drive signal to the C-Arm driver 15 and the bed driving unit 32, and controls the motions of the C-Arm 14 and the top 33 in real time. Thereby, projection data relating to the subject P is obtained.

The processing circuitry 44 generates an X-ray image with the image generation function 444. Specifically, the processing circuitry 44 generates an X-ray image using projection data output from the X-ray detector 13 of the imaging unit 10 based on a set of image quality conditions set by the imaging condition setting function 441. Thereby, an X-ray image is generated in accordance with a desired set of image quality conditions. The generated X-ray image is stored in the memory 41.

The processing circuitry 44 performs, with the image processing function 445, various types of image processing on the X-ray image. For example, the processing circuitry 44 adjusts the brightness of an X-ray image generated by the image generation function 444 based on a magnification of the automatic gain control (hereinafter referred to as "AGC") input from the input interface 43. That is, the processing circuitry 44 performs a gain correction process on the generated X-ray image. The processing circuitry 44 may perform various types of synthesis and subtraction processing on the X-ray image. The image-processed X-ray image is stored in the memory 41.

The AGC control is a digital gain process applied to the entire X-ray image if the dose of X-rays incident on the X-ray detector 13 cannot be sufficiently secured due to the limitation of exposure to the subject P and the restriction in the tube output. The magnification of AGC is defined by a ratio of a brightness of an X-ray image after AGC application to a brightness of an X-ray image before AGC application. In the present embodiment, if a halation region is present in the generated X-ray image, the processing circuitry 44 performs a gain correction process on the X-ray image to darken the halation region.

The processing circuitry 44 causes, with the display control function 446, the X-ray image to be displayed on the display 42. For example, the processing circuitry 44 acquires, based on information input from the input interface 43 and relating to an X-ray image which the operator desires to browse, an X-ray image corresponding to the information from the memory 41, and causes the display 42 to display the acquired X-ray image. The processing circuitry 44 may cause the display 42 to sequentially display X-ray images (frame images) subjected to image processing.

The processing circuitry 44 sets, with the setting function 447A, a plurality of ROIs in the X-ray image. Specifically, the processing circuitry 44 sets a plurality of ROIs in an X-ray image (first X-ray image) displayed on the display 42.

First, the processing circuitry 44 may set one of a plurality of ROIs over an entire region or a substantially entire region of the X-ray image, and set at least one of the ROIs excluding said one of the ROIs at at least one image region including at least one target photographed in the X-ray image. If, for example, a single target is photographed in the X-ray image, the processing circuitry 44 may set an ROI over an entire region or a substantially entire region of the X-ray image, and may set another ROI at a position of the single target. If two targets are photographed in an X-ray image, the processing circuitry 44 may set an ROI over an entire region or a substantially entire region of the X-ray image, and respectively set ROIs at the positions of the two targets. A plurality of ROIs may overlap one another at least partially.

Second, based on position information of a dose-reducing filter (punched filter) with an opening formed at its central part, the processing circuitry 44 may set, in an X-ray image, an image region corresponding to the opening as one of a plurality of ROIs, and set a peripheral region of the ROI as another ROI. In other words, an ROI is set at a region on an X-ray image corresponding to the opening portion of the punched filter, and another ROI may be set at a region on an X-ray image corresponding to the metal-plate portion of the punched filter.

At least one target photographed in the X-ray image is, for example, a medical device, a marker on a medical device, or an anatomical structure. Examples of the medical device include a catheter, a balloon catheter, a stent, a guide wire, a pacemaker, a transesophageal echo probe, and a prosthetic joint. Examples of the anatomical structure include bones, teeth, muscles, organs, blood vessels, and nerves. As a matter of course, at least one of the targets includes a combination of various types of such objects.

The processing circuitry 44 calculates, with the calculation function 447B, a statistical value of each of a plurality of ROIs based on a plurality of values of pixels included in each of the ROIs, thereby obtaining a plurality of statistical values. First, the processing circuitry 44 may calculate a mean value of a plurality of values of pixels included in each of the ROIs as a statistical value. Second, the processing circuitry 44 may calculate a contrast-to-noise ratio estimated based on a plurality of values of pixels included in each of the ROIs as a statistical value. For example, the processing circuitry 44 may use a mean value in ABC control, and may use a contrast-to-noise ratio estimated based on the mean value in CNR control. The statistical value may be any value calculated based on values of pixels. Specifically, the statistical value is not limited to a mean value or a contrast-to-noise ratio, and values directly calculated from values of pixels, such as a weighted mean value, an extracted value, a mode value, a median value, a maximum value, or any other values relating to the image quality such as an evaluation index may be suitably used.

"Values of pixels" means numerical values given to the respective pixels of an X-ray image. The values of pixels may be respectively given to a plurality of semiconductor detection elements (pixels) configuring an FPD included in the X-ray detector 13 of the imaging unit 10. That is, the values of pixels are values proportional to doses of X-rays that have been transmitted through the subject P. The values of pixels are represented on the display 42 in accordance with 256-level brightness values (e.g., 0-255) with, for example, a known gradation process (window process).

The processing circuitry 44 acquires, with the threshold value acquisition function 447C, a plurality of threshold values respectively relating to a plurality of statistical values. Specifically, the processing circuitry 44 acquires a plurality of threshold values from the input interface 43. The processing circuitry 44 may acquire a plurality of threshold values stored in the memory 41. Different threshold values may be given to a plurality of ROIs, or an identical threshold value may be given to at least two of the ROIs. The threshold value, which is a factor relating to determination of a dose of X-rays with which irradiation is to be performed, may also be called an "X-ray dose target value". The threshold value may be a numerical value such as "400" or "500".

The processing circuitry 44 determines, with the X-ray condition determination function 447D, a set of X-ray conditions relating to capturing of an X-ray image (second X-ray image) subsequent to an X-ray image (first X-ray image) subjected to processing, based on a statistical value and a threshold value relating to each of the ROIs. First, the processing circuitry 44 may calculate, for each of the ROIs, a set of X-ray conditions under which a statistical value satisfies a threshold value, thereby obtaining a plurality of sets of X-ray conditions, and determine, as a set of X-ray conditions relating to capturing of the second X-ray image, a set of X-ray conditions under which irradiation is performed with a highest dose of X-rays, of the plurality of sets of X-ray conditions. Second, the processing circuitry 44 may determine a set of X-ray conditions relating to capturing of the second X-ray image in such a manner that, if the number of the plurality of ROIs is two, statistical values of both of the two ROIs satisfy corresponding threshold values. Third, the processing circuitry 44 may determine a set of X-ray conditions relating to capturing of a second X-ray image in such a manner that, if the number of the plurality of ROIs is three or more, statistical values of at least two of the three or more ROIs satisfy corresponding threshold values.

In the present embodiment, the processing circuitry 44 feeds back information relating to the determined set of X-ray conditions to capturing of the next X-ray image. The processing circuitry 44 updates, with the imaging condition setting function 441, a set of X-ray conditions relating to capturing of a previous X-ray image, using the information. Hereinafter, the processing circuitry 44 sequentially executes, based on the updated set of X-ray conditions, the X-ray condition control function 442, the driving control function 443, the image generation function 444, the image processing function 445, and the display control function 446. As a result of the series of processing, a new X-ray image based on the updated set of X-ray conditions is displayed. The processing circuitry 44 sequentially executes, on the new X-ray image as a processing target, the setting function 447A, the calculation function 447B, the threshold value acquisition function 447C, and the X-ray condition determination function 447D. The above-described series of processing may be repeatedly executed over a given number of times.

FIG. 2 shows an operation example of an X-ray diagnostic apparatus 1 according to the first embodiment. The present operation example may be started in response to a start command input by the operator via the input interface 43 of the X-ray diagnostic apparatus 1. On the other hand, the present operation example may end at a given timing in response to an end command input by the operator via the input interface 43 of the X-ray diagnostic apparatus 1.

(Step S101) The X-ray diagnostic apparatus 1 sets, with the imaging condition setting function 441, imaging conditions relating to a subject P. As described above, a set of imaging conditions includes a set of X-ray conditions and a set of image quality conditions.

(Step S102) Thereafter, the X-ray diagnostic apparatus 1 irradiates, with the X-ray condition control function 442 and the driving control function 443, the subject P with X-rays based on the set of X-ray conditions set at step S101. Thereby, projection data relating to the subject P is obtained.

(Step S103) Subsequently, the X-ray diagnostic apparatus 1 generates, with the image generation function 444, an X-ray image based on a set of image quality conditions set at step S101 and projection data obtained at step S102.

(Step S104) Subsequently, the X-ray diagnostic apparatus 1 performs, with the image processing function 445, image processing on the X-ray image generated at step S103. As described above, the image processing includes a gain correction process.

(Step S105) Subsequently, the X-ray diagnostic apparatus 1 causes, with the display control function 446, the display 42 to display an X-ray image subjected to image processing at step S104. Through the above-described series of processing, an X-ray image of a subject P based on predetermined imaging conditions is captured and displayed.

(Step S106) Here, the X-ray diagnostic apparatus 1 decides, with the setting function 447A, whether or not to set ROIs in the X-ray image displayed at step S105. If the X-ray diagnostic apparatus 1 decides to set ROIs (YES at step S106), the processing advances to step S107. The X-ray diagnostic apparatus 1 may determine, for example, to set ROIs upon receiving an input operation relating to setting of ROIs from the operator. On the other hand, if the X-ray diagnostic apparatus 1 does not decide to set ROIs (NO at step S106), the processing returns to step S101. In this case, the processing from step S101 to S105 may be executed based on imaging conditions differing from the above-described predetermined imaging conditions. As a result, a new X-ray image relating to the subject P is captured and displayed.

(Step S107) Thereafter, the X-ray diagnostic apparatus 1 sets, with the setting function 447A, a plurality of ROIs in the X-ray image displayed at step S105. For example, the X-ray diagnostic apparatus 1 may automatically set a plurality of ROIs using a trained model (e.g., a neural network) that realizes an image recognition process of detecting a target. As a matter of course, the X-ray diagnostic apparatus 1 may, based on an input operation made by the operator via the input interface 43, set ROIs corresponding to the input operation. Also, the X-ray diagnostic apparatus 1 may set a plurality of ROIs using a material separation process of separating materials contained in a subject, such as spectral imaging, dual-energy technology, etc.

(Step S108) Subsequently, the X-ray diagnostic apparatus 1 calculates, with the calculation function 447B, statistical values relating to the respective ROIs based on a plurality of values of pixels included in each of the ROIs set at step S107, thereby obtaining a plurality of statistical values. As described above, in ABC control, the X-ray diagnostic apparatus 1 calculates, as a statistical value, a mean value of values of pixels of each ROI. On the other hand, in CNR control, the X-ray diagnostic apparatus 1 calculates, as a statistical value, a contrast-to-noise ratio corresponding to values of pixels of each ROI.

(Step S109) Subsequently, the X-ray diagnostic apparatus 1 acquires, with the threshold value acquisition function 447C, a threshold value relating to each of the statistical values calculated at step S108.

(Step S110) After that, the X-ray diagnostic apparatus 1 determines, with the X-ray condition determination function 447D, a set of X-ray conditions relating to an X-ray image (second X-ray image) subsequent to the X-ray image (first X-ray image) displayed at step S105, based on the statistical value and the threshold value relating to each of the ROIs calculated at steps S108 and S109. After execution of this step, the processing returns to step S101. The set of X-ray conditions determined at step S110 is fed back to the setting of the imaging conditions at step S101.

FIG. 3 shows a first example relating to setting of a plurality of ROIs and calculation of a plurality of sets of X-ray conditions by the X-ray diagnostic apparatus 1 according to the first embodiment. In an X-ray image 200A displayed by the display 42 of the X-ray diagnostic apparatus 1, two ROIs 250A and 250B are set. Moreover, the sets of X-ray conditions calculated based on the ROIs 250A and 250B are shown on the X-ray condition table 260A. The present processing may be executed inside the memory 41 or the processing circuitry 44 of the X-ray diagnostic apparatus 1.

A plurality of targets (a spine 210, a catheter 220, and a heart 230) relating to the subject P are displayed on the X-ray image 200A. Of the targets, the spine 210 and the heart 230 correspond to anatomical structures of the subject P. On the other hand, the catheter 220 corresponds to a medical device inserted into the subject P. Furthermore, dot-like radiopaque markers 220A and 220B are put on the catheter 220.

The solid lines in the X-ray image 200A show contours of targets that are displayed distinctly. On the other hand, the dashed lines in the X-ray image 200A show contours of targets that are displayed indistinctly. Also, the hatched portion in the X-ray image 200A shows an image region (i.e., a portion with a large subject thickness) that is darker than an image region on the periphery thereof. In the X-ray image 200A, the markers 220A and 220B on the catheter 220 are positioned on the outside (e.g., at a portion with a small subject thickness) of the hatched portion. Specifically, the markers 220A and 220B are positioned at the heart 230.

The X-ray diagnostic apparatus 1 sets a rectangular ROI 250A over a substantially entire region of the X-ray image 200A. Specifically, the X-ray diagnostic apparatus 1 arranges an ROI 250A in such a manner that the center of the ROI 250A matches the center of the X-ray image 200A. From a quantitative standpoint, the ROI 250A occupies approximately 80% of all the pixels configuring the X-ray image 200A. The ROI 250A includes part of the spine 210, part of the catheter 220, and part of the heart 230. The ROI 250A may also be called a general ROI.

On the other hand, the X-ray diagnostic apparatus 1 sets a circular ROI 250B so as to include markers 220A and 220B in the X-ray image 200A. Specifically, the X-ray diagnostic apparatus 1 arranges an ROI 250B inside the ROI 250A. From a quantitative standpoint, the ROI 250B occupies approximately 10% of all the pixels configuring the X-ray image 200A. The ROI 250B includes part of the catheter 220 and part of the heart 230. The ROI 250B may also be called a local ROI.

After the two ROIs 250A and 250B are set, the X-ray diagnostic apparatus 1 executes ABC or CNR control based on each of the ROIs. A given known approach may be applied to the ABC control or the CNR control. As described above, the X-ray diagnostic apparatus 1 calculates a statistical value for each ROI, and then calculates a set of X-ray conditions for each ROI based on the calculated statistical value and a threshold value corresponding to the statistical value. Thereby, a set of X-ray conditions based on each of the ROIs 250A and 250B is calculated.

According to the X-ray condition table 260A, the set of X-ray conditions calculated based on the ROI 250A is "tube voltage: A1 kV; tube current: B1 mA; pulse width: C1 msec; and beam filter: 1". On the other hand, the set of X-ray conditions calculated based on the ROI 250B are "tube voltage: A2 kV; tube current: B2 mA; pulse width: C2 msec; and beam filter: 1". Here, it is assumed that A1>A2. The X-ray diagnostic apparatus 1 compares the two sets of X-ray conditions based on the ROIs, and decides that both the value of the tube voltage kV and the irradiation dose are higher in the former set of X-ray conditions than those in the latter set of X-ray conditions. Accordingly, the X-ray diagnostic apparatus 1 determines the set of X-ray conditions based on the ROI 250A as a set of X-ray conditions relating to capturing of an X-ray image subsequent to the X-ray image 200A.

Figure 4:
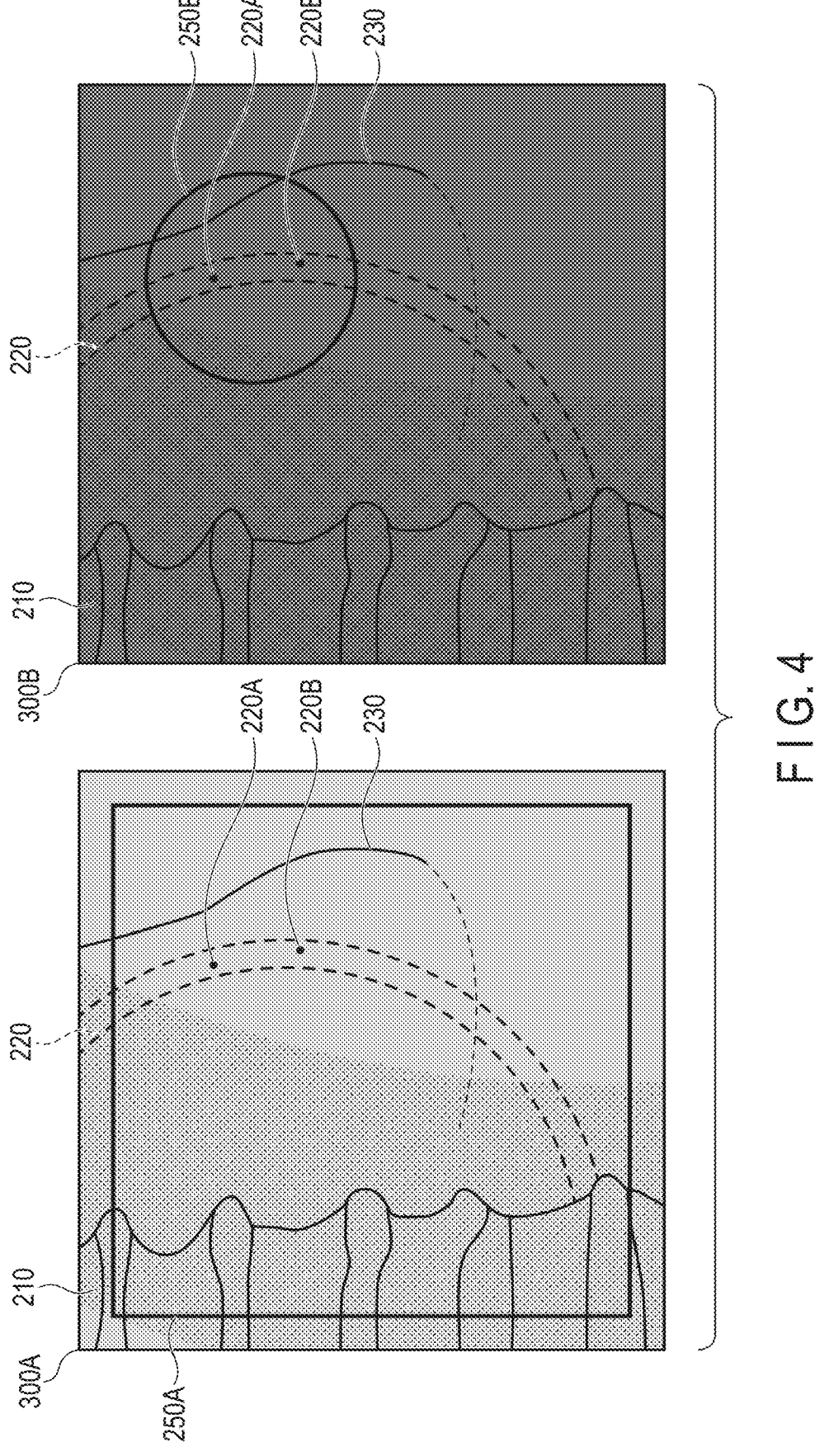
FIG. 4 shows a display example of an X-ray image based on the first example of FIG. 3.

FIG. 4 shows a display example of an X-ray image based on the first example of FIG. 3. Herein, a new X-ray image 300A based on the ROI 250A and a new X-ray image 300B based on the ROI 250B are shown. Of the two images, the X-ray image 300A is displayed on the display 42. On the other hand, the X-ray image 300B may be either displayed together with the X-ray image 300A, or not displayed.

On the X-ray images 300A and 300B, a plurality of targets relating to the subject P are displayed, similarly to the X-ray image 200A. Also, the ROI 250A used for determining the set of X-ray conditions relating to capturing of the X-ray image 300A is displayed on the X-ray image 300A. On the other hand, the ROI 250B used for determining the set of X-ray conditions relating to capturing of the X-ray image 300B is displayed on the X-ray image 300B.

When the two X-ray images are compared, it can be appreciated that the X-ray image 300A offers both a brightness of the entire image and an image visibility higher than those of the X-ray image 300B. Also, the X-ray image 300A offers a high visibility of the markers 220A and 220B on the catheter 220 compared to the X-ray image 300B. On the other hand, due to an insufficient dose, the X-ray image 300B is relatively dark in its entirety, leading to a low visibility of the markers 220A and 220B. That is, for the markers 220A and 220B in the X-ray image 200A, a set of X-ray conditions should be determined by setting a general ROI 250A, rather than by setting a local ROI 250B, to achieve a higher visibility of the markers 220A and 220B in the next X-ray image to be obtained by the determined set of X-ray conditions.

FIG. 5 shows a second example relating to setting of a plurality of ROIs and calculation of a plurality of sets of X-ray conditions by the X-ray diagnostic apparatus 1 according to the first embodiment. In an X-ray image 200B displayed by the X-ray diagnostic apparatus 1, two ROIs 250A and 250C are set. Moreover, the sets of X-ray conditions calculated based on each of the ROIs 250A and 250C are shown on the X-ray condition table 260B. A plurality of targets displayed on the X-ray image 200B are identical to the plurality of targets displayed on the X-ray image 200A. Also, the hatched portion in the X-ray image 200B shows an image region (i.e., a portion with a large subject thickness) that is darker than an image region on the periphery thereof. It is to be noted that the brightness of the entire X-ray image 200B is roughly identical to the brightness of the entire X-ray image 200A.

However, the position of the catheter 220 in the X-ray image 200B differs from the position of the catheter 220 in the X-ray image 200A. In particular, the markers 220A and 220B on the catheter 220 are positioned at the spine 210 or in the vicinity of the spine 210. The ROI 250A set in the X-ray image 200B is identical to the ROI 250A set in the X-ray image 200A.

The X-ray diagnostic apparatus 1 sets a rectangular ROI 250C so as to include markers 220A and 220B in the X-ray image 200B. Specifically, the X-ray diagnostic apparatus 1 arranges an ROI 250C inside the ROI 250A. From a quantitative standpoint, the ROI 250C occupies approximately 10% of all the pixels configuring the X-ray image 200B. The ROI 250C includes part of the spine 210 and part of the catheter 220. The ROI 250C may also be called a local ROI. The markers 220A and 220B on the catheter 220 are positioned inside the hatched portion on the X-ray image 200B (i.e., at a portion with a large subject thickness).

After the two ROIs 250A and 250C are set, the X-ray diagnostic apparatus 1 executes ABC or CNR control based on each of the ROIs. Thereby, the set of X-ray conditions based on each of the ROIs 250A and 250C is calculated.

According to the X-ray condition table 260B, the set of X-ray conditions calculated based on the ROI 250A is "tube voltage: A1 kV; tube current: B1 mA; pulse width: C1 msec; and beam filter: 1". On the other hand, the set of X-ray conditions calculated based on the ROI 250C are "tube voltage: A3 kV; tube current: B3 mA; pulse width: C3 msec; and beam filter: 1". Here, it is assumed that A1<A3. The X-ray diagnostic apparatus 1 compares the two sets of X-ray conditions based on the ROIs, and decides that both the value of the tube voltage kV and the irradiation dose are higher in the latter set of X-ray conditions than those in the former set of X-ray conditions. Accordingly, the X-ray diagnostic apparatus 1 determines the set of X-ray conditions based on the ROI 250C as a set of X-ray conditions relating to capturing of an X-ray image subsequent to the X-ray image 200B.

FIG. 6 shows a display example of an X-ray image based on the second example of FIG. 5. Herein, a new X-ray image 400A based on the ROI 250A and a new X-ray image 400B based on the ROI 250C are shown. Of the two images, the X-ray image 400B is displayed on the display 42. On the other hand, the X-ray image 400A may be either displayed together with the X-ray image 400B, or not displayed.

On the X-ray images 400A and 400B, a plurality of targets relating to the subject P are displayed, similarly to the X-ray image 200B. Also, the ROI 250A used for determining the set of X-ray conditions relating to capturing of the X-ray image 400A is displayed on the X-ray image 400A. On the other hand, an ROI 250C used for determining a set of X-ray conditions relating to capturing of the X-ray image 400B is displayed on the X-ray image 400B.

When the two X-ray images are compared, it can be appreciated that the X-ray image 400B offers both a brightness of the entire image and an image visibility higher than those of the X-ray image 400A. Also, the X-ray image 400B offers a high visibility of the markers 220A and 220B on the catheter 220 compared to the X-ray image 400A. On the other hand, due to an insufficient dose, the X-ray image 400A is relatively dark in its entirety, leading to a low visibility of the markers 220A and 220B. That is, a set of X-ray conditions should be determined by setting a local ROI 250C for the markers 220A and 220B in the X-ray image 200B, rather than by setting a general ROI 250A, to achieve a higher visibility of the markers 220A and 220B in the next X-ray image obtained by the determined set of X-ray conditions.

FIG. 7 shows an example of gain correction of an X-ray image upon occurrence of a halation. In the X-ray images 300A and 400B generated under a set of X-ray conditions under which the irradiation dose is high, a phenomenon in which the values of pixels are saturated (halation) may occur in part of the image region. Thus, if a halation region exists in part of the X-ray image, the X-ray diagnostic apparatus 1 performs a gain correction process to decrease the values of pixels of the halation region by a single level. With such a configuration of the X-ray diagnostic apparatus 1, it is possible to provide an X-ray image capable of easily identifying a target present in a halation region.

It is assumed, for example, that a halation region (white circle) has occurred at positions of the markers 220A and 220B in the X-ray image 300A (left). At this time, the X-ray diagnostic apparatus 1 applies a gain correction process to the X-ray image 300A. Thereby, the markers 220A and 220B are displayed on the display 42 in a recognizable manner in the gain-corrected X-ray image 300A (right).

The X-ray diagnostic apparatus 1 according to the first embodiment has been described above. The X-ray diagnostic apparatus 1 sets a plurality of ROIs in an X-ray image, and determines, based on a statistical value and a threshold value relating to each of the ROIs, a set of X-ray conditions relating to capturing of an X-ray image subsequent to the X-ray image. With such a configuration of the X-ray diagnostic apparatus 1, it is possible to determine a more appropriate set of X-ray conditions as compared to the method of determining a set of X-ray conditions based on a single ROI. Accordingly, with the X-ray diagnostic apparatus 1, it is possible to avoid a situation in which a dose to the entire X-ray image becomes insufficient, causing a decrease in visibility of the X-ray image, as shown in the X-ray images 300B and 400A. Rather, with the X-ray diagnostic apparatus 1, it is possible to provide an X-ray image with high visibility by securing a sufficient dose for the entire X-ray image, as shown in the X-ray images 300A and 400B. Also, with the X-ray diagnostic apparatus 1, it is possible to provide an optimum X-ray image, taking into consideration both visibility (image quality) relating to a local ROI on the X-ray image and visibility (image quality) relating to the general ROI on the X-ray image.

Moreover, the X-ray diagnostic apparatus 1 according to the first embodiment may set one of a plurality of ROIs over an entire region or a substantially entire region of an X-ray image, and set at least one ROI excluding said one of the ROIs at an image region including a target photographed in the X-ray image. With such a configuration of the X-ray diagnostic apparatus 1, it is possible to maintain or improve visibility relating to both the entire region or the substantially entire region of the X-ray image and the image region including the target in the X-ray image.

Furthermore, the X-ray diagnostic apparatus 1 according to the first embodiment may estimate, based on a plurality of values of pixels included in each of a plurality of ROIs, an image quality index (e.g., a contrast-to-noise ratio) of each of the ROIs, and calculate the estimated image quality index as a statistical value. For example, the X-ray diagnostic apparatus 1 may calculate, using a plurality of values of pixels included in a single ROI, a mean value of the values of pixels, and converts the calculated mean value into a water-equivalent thickness. Subsequently, the X-ray diagnostic apparatus 1 may convert the water-equivalent thickness into a contrast-to-noise ratio via a lookup table, etc. The X-ray diagnostic apparatus 1 may use the mean value, the contrast-to-noise ratio, or the like calculated by the above-described series of processing as a statistical value relating to the ROI. In this case, with the X-ray diagnostic apparatus 1, it is possible to maintain or improve visibility relating to each of the ROIs represented by the statistical value. That is, the statistical value may be a scale or index of the visibility of each ROI.

Moreover, the X-ray diagnostic apparatus 1 according to the first embodiment may obtain a plurality of sets of X-ray conditions by calculating, for each of a plurality of ROIs, a set of X-ray conditions under which a statistical value satisfies a threshold value, and set, as a set of X-ray conditions relating to capturing of a next X-ray image, a set of X-ray conditions under which irradiation is performed with a highest dose of X-rays, of the plurality of sets of X-ray conditions. With such a configuration of the X-ray diagnostic apparatus 1, it is possible to capture and display an X-ray image with a higher brightness.

Furthermore, the X-ray diagnostic apparatus 1 according to the first embodiment may determine a set of X-ray conditions relating to capturing of a next X-ray image in such a manner that, if the number of a plurality of ROIs is two, statistical values of both of the two ROIs satisfy corresponding threshold values. With such a configuration of the X-ray diagnostic apparatus 1, it is possible to maintain or improve visibility relating to both of the two ROIs.

Moreover, the X-ray diagnostic apparatus 1 according to the first embodiment may determine a set of X-ray conditions relating to capturing of a next X-ray image in such a manner that, if the number of a plurality of ROIs is three or more, statistical values of at least two of the three or more ROIs satisfy corresponding threshold values. With such a configuration of the X-ray diagnostic apparatus 1, it is possible to maintain or improve visibility relating to the at least two ROIs.

Furthermore, the X-ray diagnostic apparatus 1 according to the first embodiment may perform, if a halation region is present in an X-ray image generated based on a determined set of X-ray conditions, a gain correction process on the X-ray image to darken the halation region. With such a configuration of the X-ray diagnostic apparatus 1, it is possible to decrease a brightness of the halation region that has occurred by X-ray irradiation under a set of X-ray conditions under which a dose of X-ray irradiation is relatively high, thereby maintaining or improving visibility relating to the halation region.

Moreover, the X-ray diagnostic apparatus 1 according to the first embodiment may, based on position information of a dose-reducing filter (punched filter) with an opening formed at its central part, set an image region in an X-ray image corresponding to the opening as one of the ROIs, and set a peripheral region of the ROI as another ROI. With such a configuration of the X-ray diagnostic apparatus 1, it is possible to maintain or improve visibility relating to both the image region corresponding to the opening portion of the beam filter and an image region corresponding to a metal-plate portion of the beam filter. As a result, with the X-ray diagnostic apparatus 1, it is possible to avoid a situation in which visibility of a medical device, etc. substantially decreases due to an insufficient dose to an image region overlapping the dose-reducing filter.

Furthermore, the X-ray diagnostic apparatus 1 according to the first embodiment is configured to set an ROI at an image region including a target photographed in an X-ray image. With such a configuration of the X-ray diagnostic apparatus 1, it is possible to maintain or improve visibility relating to the ROI including the target.

Second Embodiment

Hereinafter, an X-ray diagnostic apparatus 1 according to the second embodiment will be described. The X-ray diagnostic apparatus 1 according to the second embodiment sets priorities for a plurality of ROIs. The X-ray diagnostic apparatus 1 secures a required dose for an ROI for which a highest priority is set, while securing a minimum dose for ROIs for which second highest and subsequent priorities are set. To realize such processing, the processing circuitry 44 according to the second embodiment performs the processing shown below. The other configuration is similar to that of the first embodiment.

The processing circuitry 44 sets, with the setting function 447A, a priority for each of the ROIs. The processing circuitry 44 calculates, with the calculation function 447B, a statistical value relating to each of the ROIs based on a plurality of values of pixels included in each of the ROIs for which priorities are set, thereby obtaining a plurality of statistical values. The processing circuitry 44 acquires, with the threshold value acquisition function 447C, a maximum value and a minimum value relating to corresponding threshold values of the statistical values.

The processing circuitry 44 determines, with the X-ray condition determination function 447D, a set of X-ray conditions relating to capturing of a next X-ray image in such a manner that a statistical value of an ROI with a highest priority of a plurality of ROIs falls in a range between a threshold value and a maximum value, and a statistical value of at least one of the ROIs excluding the ROI with the highest priority falls in a range between the threshold value and a minimum value.

FIG. 8 shows an operation example of the X-ray diagnostic apparatus 1 according to the second embodiment. Similarly to the first embodiment, the present operation example may be started in response to a start command, and may end in response to an end command.

(Steps S201-S205) First, the X-ray diagnostic apparatus 1 performs processing similar to steps S101 to S105 of the first embodiment. Thereby, an X-ray image relating to a subject P based on predetermined imaging conditions is captured and displayed.

(Step S206) Here, the X-ray diagnostic apparatus 1 decides, with the setting function 447A, whether or not to set ROIs in the X-ray image displayed at step S205. Step S206 is similar to step S106.

(Step S207) Thereafter, the X-ray diagnostic apparatus 1 sets, with the setting function 447A, a plurality of ROIs in an X-ray image displayed at step S205. Step S207 is similar to step S107.

(Step S208) Subsequently, the X-ray diagnostic apparatus 1 sets, with the setting function 447A, priorities for the respective ROIs set at step S207. For example, the X-ray diagnostic apparatus 1 sets, as an ROI with a highest priority, one of the ROIs including at least one target photographed in the X-ray image. Specifically, the X-ray diagnostic apparatus 1 may set a highest priority (priority 1) for a local ROI including a medical device, to which the operator is highly likely to be currently paying attention. Also, the X-ray diagnostic apparatus 1 may set a second highest priority (priority 2) for an ROI set over an entire region or a substantially entire region of the X-ray image. Alternatively, the X-ray diagnostic apparatus 1 may set a second highest priority (priority 2) for a local ROI including a medical device, to which the operator is less likely to be currently paying attention. Different priorities may be set for a plurality of ROIs, or an identical priority may be set for at least two of the ROIs.

(Step S209) Subsequently, the X-ray diagnostic apparatus 1 calculates, with the calculation function 447B, a statistical value relating to each of the ROIs based on a plurality of values of pixels included in each of the ROIs set at step S207, thereby obtaining a plurality of statistical values. Step S209 is similar to step S108.

(Step S210) Subsequently, the X-ray diagnostic apparatus 1 acquires, with the threshold value acquisition function 447C, a maximum value and a minimum value relating to a threshold value of each of the statistical values calculated at step S209. The X-ray diagnostic apparatus 1 may acquire the maximum value and the minimum value of each threshold value from the input interface 43, or acquire the maximum value and the minimum value of each threshold value stored in the memory 41. The maximum value of the threshold value defines, for example, the maximum value of the irradiation dose of X-rays. On the other hand, the minimum value of the threshold value defines, for example, the minimum value of the irradiation dose of X-rays.

(Step S211) After that, the X-ray diagnostic apparatus 1 determines, with the X-ray condition determination function 447D, a set of X-ray conditions relating to an X-ray image (second X-ray image) subsequent to the X-ray image (first X-ray image) displayed at step S205, based on the priority, the statistical value, the threshold value, the maximum value, and the minimum value relating to each of the ROIs calculated at steps S208 to S210. For example, the X-ray diagnostic apparatus 1 determines a set of X-ray conditions relating to capturing of the second X-ray image in such a manner that a statistical value of an ROI with a highest priority falls in a range between a threshold value and a maximum value, and a statistical value of at least one of the ROIs excluding the ROI with the highest priority falls in a range between the threshold value and a minimum value. After execution of this step, the processing returns to step S201. The set of X-ray conditions determined at step S211 is fed back to the setting of the imaging conditions at step S201.

The X-ray diagnostic apparatus 1 according to the second embodiment has been described above. With the X-ray diagnostic apparatus 1 according to the second embodiment, it is possible to obtain advantageous effects similar to those of the first embodiment. With the X-ray diagnostic apparatus 1 according to the second embodiment, it is possible to secure a sufficient dose for obtaining a statistical value between the threshold value and the maximum value for the ROI with the highest priority, and to secure a required minimum dose for obtaining a statistical value between the threshold value and the minimum value for the ROI with a second highest priority. With the X-ray diagnostic apparatus, it is possible to secure a minimum dose for each of the ROIs with the third highest and subsequent priorities. It is thus possible, with the X-ray diagnostic apparatus 1, to optimize a dose of irradiation to the subject P.

Moreover, the X-ray diagnostic apparatus 1 according to the second embodiment may set, as an ROI with a highest priority, one of the ROIs including at least one target photographed in an X-ray image. With such a configuration of the X-ray diagnostic apparatus 1, it is possible to secure a sufficient dose for the ROI including the target, thereby maintaining or improving the visibility relating to the ROI.

Another Embodiment

The X-ray diagnostic apparatus 1 according to another embodiment may determine a set of X-ray conditions according to an imaging mode selected by the operator (e.g., a Dynamic Trace mode, a stent enhancement mode, etc.). If, for example, a stent enhancement mode is selected, the X-ray diagnostic apparatus 1 changes the tube voltage kV and the type of the beam filter for improving the contrast of the medical device. Thereafter, the X-ray diagnostic apparatus 1 adjusts the pulse width msec in accordance with a movement, a portion, etc. of the subject P per frame image. Subsequently, the X-ray diagnostic apparatus 1 adjusts the tube current mA. In this manner, the X-ray diagnostic apparatus 1 may set parameters defining a set of X-ray conditions in accordance with a predetermined order.

Moreover, the X-ray diagnostic apparatus 1 may switch to a real-time display of a local ROI and a general ROI in accordance with the position of the local ROI set on an X-ray image. If, for example, a local ROI has moved from a dark region to a bright region on the X-ray image, the X-ray diagnostic apparatus 1 calculates a set of X-ray conditions based on the local ROI after the movement, and calculates a set of X-ray conditions based on the general ROI. If an X-ray dose based on the latter set of X-ray conditions is higher than an X-ray dose based on the former set of X-ray conditions, the X-ray diagnostic apparatus 1 may switch the ROI to be displayed from the local ROI to the general ROI. Conversely, if the X-ray dose based on the former set of X-ray conditions is higher than the X-ray dose based on the latter set of X-ray conditions, the X-ray diagnostic apparatus 1 may switch the ROI to be displayed from the general ROI to the local ROI. Through such an operation, the X-ray diagnostic apparatus 1 can present in real time which of the local ROI and the general ROI the displaying of the X-ray image is based on.

Furthermore, in automatically setting ROIs, the X-ray diagnostic apparatus 1 may recognize an anatomical structure of the subject P or a marker on a medical device photographed in the X-ray image, and set ROIs based on the recognized result. For example, the X-ray diagnostic apparatus 1 may set ROIs based on a result of material differentiation in a plurality of images in a single pulse obtained by the dual-energy technology using two different types of tube voltages. Alternatively, the X-ray diagnostic apparatus 1 may recognize a target photographed in the X-ray image by classifying the pixels in the X-ray image using a trained model (e.g., semantic segmentation) based on AI technology, and sets ROIs based on the recognized result.

That is, when the X-ray diagnostic apparatus 1 recognizes an anatomical structure of the subject or a maker on a medical device, a system based on the dual-energy technology and a system based on an AI-technology-based segmentation process can be used. Moreover, the X-ray diagnostic apparatus 1 can set ROIs in accordance with a result of recognition by material differentiation.

Moreover, the X-ray diagnostic apparatus 1 may set ROIs based on a recognition result obtained by material differentiation, and set a threshold value for each ROI. If, for example, a bone of a subject is recognized by material differentiation, the X-ray diagnostic apparatus 1 may set a threshold value of an ROI set at the bone to be lower than threshold values of the other ROIs. With such a configuration of the X-ray diagnostic apparatus 1, it is possible to suppress an occurrence of halation in the other ROIs caused by an increase in brightness of the ROI set at the bone.

Furthermore, the X-ray diagnostic apparatus 1 may set a plurality of ROIs based on a recognition result obtained by material differentiation, and set priorities to the ROIs. If, for example, a bone and an organ of the subject and a marker on a medical device are recognized by material differentiation, the X-ray diagnostic apparatus 1 may set a highest priority to an ROI set at the marker, and set a second or third priority to an ROI set at the bone. If the third highest priority is set to the ROI set at the bone, the X-ray diagnostic apparatus 1 may set the second highest priority to an ROI set over a substantially entire region of the X-ray image. In this manner, the X-ray diagnostic apparatus 1 automatically sets priorities to a plurality of ROIs based on a recognition result obtained by material differentiation, thereby omitting the operator's burden of manually setting priorities to the ROIs.

Hereinafter, a method of setting ROIs according to another embodiment will be described. First, the X-ray diagnostic apparatus 1 may set ROIs in an X-ray image of a subject in accordance with an examination protocol of each anatomical site (e.g., a heart, an abdomen, a head, etc.) of the subject. Second, the X-ray diagnostic apparatus 1 may set ROIs in the X-ray image of the subject in response to the operator's operation.

Setting of ROIs in an X-ray image by the X-ray diagnostic apparatus 1 may be performed by a combination of the above-described first and second methods. For example, the X-ray diagnostic apparatus 1 automatically sets an ROI A in an X-ray image of a subject in accordance with an examination protocol of the subject. Subsequently, in response to the operator's operation, the X-ray diagnostic apparatus 1 may add another ROI B to the X-ray image, or edit and delete the ROI A.

FIG. 9 shows an example of a method of setting a plurality of ROIs according to another embodiment. An X-ray image 200C shown in FIG. 9 is similar to the X-ray image 200B shown in FIG. 5. The X-ray diagnostic apparatus 1 sets ROIs 250P, 250Q, and 250C in the X-ray image 200C in response to the operator's operation. As a matter of course, the X-ray diagnostic apparatus 1 may calculate a set of X-ray conditions based on each of the ROIs 250P, 250Q, and 250C.

Specifically, the X-ray diagnostic apparatus 1 sets an ROI 250P at a left half of the X-ray image 200C, and sets an ROI 250Q at a right half of the X-ray image 200C. On the other hand, the X-ray diagnostic apparatus 1 sets an ROI 250C at a target (e.g., markers 220A and 220B) of the X-ray image 200C. With such a configuration of the X-ray diagnostic apparatus 1, it is possible to set ROIs in a target in response to the operator's operation, even if the target cannot be detected by an image recognition process, etc.

According to at least one of the above-described embodiments, it is possible to improve visibility of the X-ray image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to:
  set a plurality of regions of interest (ROIs) in a first X-ray image;
  set a priority to each of the ROIs;
  calculate a statistical value relating to each of the ROIs based on a plurality of values of pixels included in each of the ROIs, thereby obtaining a plurality of statistical values;
  acquire a threshold value relating to each of the statistical values;
  acquire a maximum value and a minimum value relating to the threshold value of each of the statistical values; and
  determine a set of X-ray conditions relating to capturing of a second X-ray image subsequent to the first X-ray image in such a manner that the statistical value of a ROI with a highest priority among the ROIs falls in a range between the threshold value and the maximum value, and the statistical value of at least one of the ROIs excluding the ROI with the highest priority falls in a range between the threshold value and the minimum value.

2. The X-ray diagnostic apparatus according to claim 1, wherein the processing circuitry is further configured to set the plurality of ROIs based on a user's input.

3. The X-ray diagnostic apparatus according to claim 1, wherein the processing circuitry is further configured to set one of the ROIs over an entire region or a substantially entire region of the first X-ray image, and set at least one of the ROIs excluding said one of the ROIs at at least one image region including at least one target photographed in the first X-ray image.

4. The X-ray diagnostic apparatus according to claim 1, wherein the processing circuitry is further configured to calculate, for each of the ROIs, a set of X-ray conditions under which the statistical value satisfies the threshold value, thereby obtaining a plurality of sets of X-ray conditions, and determine, as the set of X-ray conditions relating to capturing of the second X-ray image, a set of X-ray conditions under which irradiation is performed with a highest dose of X-rays, of the plurality of sets of X-ray conditions.

5. The X-ray diagnostic apparatus according to claim 1, wherein
the plurality of ROIs are two ROIs, and
the processing circuitry is further configured to determine the set of X-ray conditions relating to capturing of the second X-ray image in such a manner that the statistical value of each of the two ROIs satisfies the threshold value.

6. The X-ray diagnostic apparatus according to claim 1, wherein
the plurality of ROIs are three or more ROIs, and
the processing circuitry is further configured to determine the set of X-ray conditions relating to capturing of the second X-ray image in such a manner that the statistical value of each of at least two of the three or more ROIs satisfies the threshold value.

7. The X-ray diagnostic apparatus according to claim 1, wherein the processing circuitry is further configured to set, as the ROI with the highest priority, one of the ROIs including at least one target photographed in the first X-ray image.

8. The X-ray diagnostic apparatus according to claim 1, wherein the processing circuitry is further configured to calculate, as the statistical value, at least one of a mean value relating to the plurality of values of pixels included in each of the ROIs and an image quality index estimated based on the plurality of values of pixels.

9. The X-ray diagnostic apparatus according to claim 8, wherein the image quality index includes a contrast-to-noise ratio.

10. The X-ray diagnostic apparatus according to claim 1, wherein the processing circuitry is further configured to perform, if a halation region is present in the second X-ray image generated based on the determined set of X-ray conditions, a gain correction process on the second X-ray image to darken the halation region.

11. The X-ray diagnostic apparatus according to claim 1, further comprising:
  an X-ray tube configured to generate X-rays; and
  an X-ray attenuation filter arranged between the X-ray tube and a subject, including an opening configured to let X-rays for irradiating the subject pass through without reducing the X-rays, and including a dose-reducing portion arranged on a periphery of the opening and configured to reduce the X-rays,
wherein the processing circuitry is further configured to set, in the first X-ray image, an image region corresponding to the opening as one of the ROIs based on position information of the opening, and sets a peripheral region of said one of the ROIs as another ROI.

12. The X-ray diagnostic apparatus according to claim 1, wherein
  at least one target photographed in the first X-ray image includes at least one of a medical device, a marker on the medical device, and an anatomical structure,
  the medical device includes at least one of a catheter, a balloon catheter, a stent, a guide wire, a pacemaker, a transesophageal echo probe, and a prosthetic joint, and
  the anatomical structure includes at least one of a bone, a tooth, a muscle, an organ, a blood vessel, and a nerve.

13. An X-ray condition determination method performed by processing circuitry, the method comprising:
  setting a plurality of regions of interest (ROIs) in a first X-ray image;
  setting a priority to each of the ROIs;
  calculating a statistical value relating to each of the ROIs based on a plurality of values of pixels included in each of the ROIs, thereby obtaining a plurality of statistical values;
  acquiring a threshold value relating to each of the statistical values;
  acquiring a maximum value and a minimum value relating to the threshold value of each of the statistical values; and
  determining a set of X-ray conditions relating to capturing of a second X-ray image subsequent to the first X-ray image in such a manner that the statistical value of a ROI with a highest priority among the ROIs falls in a range between the threshold value and the maximum value, and the statistical value of at least one of the ROIs excluding the ROI with the highest priority falls in a range between the threshold value and the minimum value.

14. A non-transitory computer-readable medium having recorded thereon a plurality of computer-executable instructions that cause the computer to execute the steps of:
  setting a plurality of regions of interest (ROIs) in a first X-ray image;
  setting a priority to each of the ROIs;

calculating a statistical value relating to each of the ROIs based on a plurality of values of pixels included in each of the ROIs, thereby obtaining a plurality of statistical values;

acquiring a threshold value relating to each of the statistical values;

acquiring a maximum value and a minimum value relating to the threshold value of each of the statistical values; and determining a set of X-ray conditions relating to capturing of a second X-ray image subsequent to the first X-ray image in such a manner that the statistical value of a ROI with a highest priority among the ROIs falls in a range between the threshold value and the maximum value, and the statistical value of at least one of the ROIs excluding the ROI with the highest priority falls in a range between the threshold value and the minimum value.

15. The X-ray condition determination method according to claim 13, further comprising:

setting the plurality of ROIs based on a user's input.

16. The X-ray condition determination method according to claim 13, further comprising:

setting one of the ROIs over an entire region or a substantially entire region of the first X-ray image; and setting at least one of the ROIs excluding said one of the ROIs at at least one image region including at least one target photographed in the first X-ray image.

17. The X-ray condition determination method according to claim 13, further comprising:

calculating, for each of the ROIs, a set of X-ray conditions under which the statistical value satisfies the threshold value, thereby obtaining a plurality of sets of X-ray conditions; and determining, as the set of X-ray conditions relating to capturing of the second X-ray image, a set of X-ray conditions under which irradiation is performed with a highest dose of X-rays, of the plurality of sets of X-ray conditions.

18. The X-ray condition determination method according to claim 13, further comprising:

setting, as the ROI with the highest priority, one of the ROIs including at least one target photographed in the first X-ray image.

* * * * *